| United States Patent [19] | [11] Patent Number: 4,582,790 |
| Auerbach | [45] Date of Patent: Apr. 15, 1986 |

[54] MONOCLONAL ANTIBODY TO ANGIOTENSION-CONVERTING ENZYME AND METHODS OF PREPARING AND USING SAME

[75] Inventor: Robert Auerbach, Middleton, Wis.

[73] Assignee: Wisconsin Alumni Research Foundation, Madison, Wis.

[21] Appl. No.: 466,477

[22] Filed: Feb. 15, 1983

[51] Int. Cl.$^4$ .................... G01N 33/535; C12N 15/00
[52] U.S. Cl. .......................................... 435/7; 435/68; 435/172.2; 435/240
[58] Field of Search ................... 435/7, 68, 172.2, 240

[56] References Cited

U.S. PATENT DOCUMENTS

| 4,196,265 | 4/1980 | Koprowski et al. | 435/172.2 |
| 4,381,295 | 4/1983 | Kung et al. | 435/7 |
| 4,487,829 | 12/1984 | Sharp et al. | 435/172.2 |

OTHER PUBLICATIONS

Auerbach et al. –Microvascular Research, vol. 29 (1985) pp. 401–411.

Auerbach et al., –Proc. Nat. Acad. Sci.; vol. 79 (Dec. 1982) pp. 7891–7895.

*Primary Examiner*—Sam Rosen
*Attorney, Agent, or Firm*—David J. Houser

[57] ABSTRACT

A method for preparing a monoclonal antibody of improved cross-species specificity. The method includes the steps of preparing an inoculum antigen from a first species of animal producing the antigen and then immunizing a selected subject animal with the inoculum antigen. The method further includes the steps of fusing spleen cells from the immunized subject animal with myeloma cells to produce hybridomas. A test antigen is prepared corresponding to the inoculum antigen but derived from a second species of animal, distinct from the first species of animal from which the inoculum antigen was prepared. Hybridomas are screened for desired antibody production against the test antigen. The hybridoma producing antibodies most active against the test antigen is then cultured, and monoclonal antibodies are produced therefrom.

47 Claims, No Drawings

MONOCLONAL ANTIBODY TO ANGIOTENSION-CONVERTING ENZYME AND METHODS OF PREPARING AND USING SAME

This invention was made with United States Government support under NIH Grant Nos. 5-RO1-AI 14607-04; 5-RO1-EY 03 243-01; 5-RO1-EY 03 243-02; 1-RO1 CA2 8656-01A1; and 1 T32HDO7118 awarded by the Department of Health and Human Services. The United States Government has certain rights in this invention.

TECHNICAL FIELD

This invention relates generally to a new method of preparing a hybrid cell line adapted to produce monoclonal antibodies of improved cross-species specificity, and, more specifically, to the preparation and use of a monoclonal antibody to angiotensin-converting enzyme having such improved cross-species specificity.

BACKGROUND OF THE ART

The art is generally cognizant of the basic technique of fusing mouse myeloma cells to spleen cells from immunized mice to obtain a culturable, continuous cell line making homogeneous or "monoclonal" antibodies. See, for example Kohler and Milstein, Nature 256, 495–497 (1975). However, particular difficulties and unique requirements are frequently encountered in attempts to apply this general knowledge, and even if hybridomas are successfully produced, there is no assurance that one will be obtained that produces an antibody having a desired specificity.

In the production of monoclonal antibodies and the hybridomas making them, a convenient experimental animal, such as a mouse, is exposed to the antigen against which an antibody is desired. Typically, some of the antigen is injected into the animal, and its immune system is allowed to respond to it. This process may be repeated until the animal's immune system is presumed to be producing antibodies to the antigen, as well as such other antibodies as the animal may be producing without regard to the injections of the antigen. The animal is then killed, and antibody-producing cells from it are isolated. Typically spleen cells from the animal are employed.

A large number of such spleen cells are then fused with myeloma cells of the same species to obtain hybrid cells that will reproduce without the self-limiting growth characteristics of most non-tumor cells. The fused cells are then cultured as cell lines of genetically identical, antibody producing cells. However, there is no assurance that the antibody produced by any particular cell line is an antibody to the original antigen or that the antibody will be specific to the antigen.

In order to select from among the many hybridoma cell lines thus produced for a particular cell line that produces a desired antibody, it is necessary to screen the cell lines. Typically this is done by testing the antibody produced by each cell line against the original antigen or a purified form thereof. The cell lines that are found by this means to produce a desired antibody are then preserved, and the remainder are discarded.

Many antigens are complex and may be species specific in at least certain respects. Thus, if mouse cells of a given type are used as the antigen in the process reviewed above, the antibody produced by a resulting hybridoma may be specific to any of many antigenic features of such cells or combinations of such features. If, for example, endothelial cells are employed, the antibody produced may be to an antigenic feature typical of endothelial cells in general, of mouse endothelial cells, of mouse cells regardless of their origin, and so forth. There is no assurance whatsoever that the antibody will be specific against endothelial cells of other species. Even within a given species, it has been shown that antibodies specific to endothelial cells taken from a given organ or tissue may not react in the same way to like cells from other organs or tissues. See J. Joseph, et al., Endothelial Cell Identification and Culture Methods, D. Thilo, ed., Karger, Basel (in press).

Certain enzymes, especially when in situ on cells, may also constitute antigens of sufficient complexity that a monoclonal antibody produced against the antigen has an unpredictable specificity. Thus, enzymes operating on a like substrate but produced by different species may differ sufficiently in themselves and certainly in the way they are presented by the cells of each species that a monoclonal antibody developed against the enzyme as produced or situated in the mouse, for example, may not react with the corresponding enzyme as produced or situated in bovine or human cells. A monoclonal antibody to such an enzyme may recognize the enzyme only in the context of aspects of a cell that are species specific instead of recognizing the parts that relate solely to the substrate acted on by the enzyme. And, as mentioned above, parts of the enzyme itself may be species specific. For reasons of efficiency and flexibility, it is desirable to be able to produce monoclonal antibodies usable in assays and similar work that are specific to an enzyme without being excessively specific to the species source of the cell presenting the enzyme.

It should be emphasized again that the unpredictable nature of hybrid cell preparation generally does not allow one to extrapolate from one antigen or cell system to another to predict precise outcomes of the application of conventional hybridization techniques. The successful production of an antibody of effective cross-species specificity produced by a hybridoma generated in response to inoculation with antigen from a given species is even more incapable of prediction.

Angiotensin-converting enzymes (hereinafter "ACE") are produced by many species. It is unknown if ACE is the same in all species or differs from species to species. In any event, there is no way to predict the ability of an antibody to react to the ACE of different species in situ on endothelial cells. However, ACE as produced by each such species, functions in known ways to convert the decapeptide angiotensin I to an octapeptide angiotensin II. See Ryan, et al., U.S. Pat. No. 4,115,374.

Detecting the presence and levels of ACE itself has medical utility, as is discussed in Ryan, et al. Furthermore, the endothelial cells of species producing ACE may be distinguished from other cells of those organisms in that the endothelial cells interact with the ACE produced by the organism. The ACE becomes bound to the surface of the endothelial cells. Thus, an antibody specific to ACE becomes an effective way to distinguish endothelial cells. This is desirable as a tool in the operation of fluorescence actuated cell sorters and like assay and separation techniques and equipment. The antibody to ACE may be directly labeled in conventional ways for detection by radiological, fluorescent, enzyme reaction, or other means. Alternatively, the antibody to ACE may be itself unlabeled but be subjected to reaction with another, labeled antibody. Thus, if the original antibody to ACE was produced by a mouse, commercially available preparations of labeled goat anti-mouse or rabbit anti-mouse antibodies could be employed. The presence of such labeled antibodies may then be detected by conventional means to indirectly reveal the presence of the antibody to ACE.

In the past, production of anti-ACE antibodies has been possible by conventional inoculation of rabbits or other animals and the processing of serum later extracted from the inoculated animal. The attempted production of a monoclonal antibody to ACE has not been reported, much less the production of such an antibody having effective cross-species specificity.

SUMMARY OF THE INVENTION

The present invention is summarized in that a method for preparing a monoclonal antibody of improved cross species specificity includes the steps of preparing an inoculum antigen from a first species of animal producing the antigen and immunizing a selected subject animal with the inoculum antigen. The method further includes the steps of fusing spleen cells from the immunized subject animal with myeloma cells to produce hybridomas. A test antigen is prepared corresponding to the inoculum antigen but derived from a second species of animal different from the first species of animal from which the inoculum antigen was prepared. Hybridomas are screened for desired antibody production against the test antigen. The hybridoma producing antibodies most active against the test antigen is then cultured, and monoclonal antibodies are produced therefrom.

The invention is further summarized in that a method of preparing monoclonal antibody that reacts both with purified ACE and mouse, bovine, and human endothelial cells includes the steps of culturing the hybridoma ATCC HB 8191 in a suitable medium and recovering the antibody from the supernatant above the hybridoma.

The invention is further summarized in that a method of preparing monoclonal antibody that reacts both with purified ACE and mouse, bovine, and human endothelial cells includes injecting into a mouse the hybridoma ATCC HB 8191 and recovering the antibody from one of the malignant ascites and serum of the mouse.

A primary object of the invention is to provide a monoclonal antibody to ACE.

A second object of the invention is to provide such an antibody effective in recognizing ACE when it is bound to the surface of endothelial cells.

A further object of the invention is to provide such an antibody that exhibits effective, cross-species specificity to endothelial cells bearing ACE.

Yet another object of the invention is to provide a method for obtaining a hybridoma cell line capable of producing a monoclonal antibody having effective cross-species specificity.

Yet another object of the invention is to produce an antibody that can be used in flow cytometry and other assay and separation techniques to detect and separate endothelial cells from nonendothelial cells and ACE from other materials with good cross-species specificity.

Other objects and advantages of the invention will be apparent from the following detailed description setting forth the preferred embodiment of the invention.

DETAILED DESCRIPTION OF THE PREFERRED EMBODIMENT

In general overview, the method of the invention for preparing a monoclonal antibody of improved cross-species specificity includes immunizing a selected subject animal, such as a mouse, with inoculum antigen derived from a first species of animal producing the antigen. Spleen cells from the subject animal are then fused by conventional means described more fully below with myeloma cells to produce hybridomas. The hybridomas are then screened for desired antibody production. To accomplish this screening, the hybridomas are isolated and preferably are grown in conventional ways until sufficient amounts are available for subsequent procedures. Antibodies produced by each hybridoma are tested for antibody activity against a test antigen. The test antigen is derived from a second species of animal, different from the first species from which the inoculum antigen was derived. The hybridoma selected by this screening procedure is then cultured as a hybrid cell line adapted to produce monoclonal antibodies having improved cross-species specificity.

In order to describe the invention in greater detail and provide a typical instance of its application, the production of a monoclonal antibody against angiotensin-converting enzyme will be described in the Example below in which the monoclonal antibody produced has improved cross-species specificity. An ACE preparation was obtained from rat lung. The ACE thus obtained was used as an inoculum antigen in the immunization of BALB/c mice. Spleen cells from the mice so immunized were fused with myeloma cells, fusion being effected with treatment in polyethylene glycol in accord with known methods. Resulting hybridomas were cultured and then screened for antibody activity. Hybridoma supernatents were tested for binding to the ACE associated with the surface of bovine pulmonary endothelial cells by means of an enzyme-linked immunosorbent assay (hereinafter "ELISA"), in the manner well known in the art. The hybridoma so selected was found to be an IgM-producing clone. Multi-species cell binding studies were carried out by using ELISAs and flow cytometry. The antibody produced by the hybridoma was found to be specific to ACE associated endothelial cells taken from adult and fetal bovine materials, mouse endothelial materials, and human endothelial materials, as well as to purified bovine ACE.

EXAMPLE

Preparation of Inoculum Antigen

ACE for use as an inoculum antigen was obtained following the methods of Lanzillo and Fanburg, *J. Biol. Chem.* 249, 2312-2318 (1974); *Biochemistry* 16, 5491-5495 (1977). In brief, rat lungs were dissected after lavage, lightly homogenized in 0.02 M potassium phosphate buffer (pH 8.3), and centrifuged (250 x g; 10 min.) to remove cells and debris. The supernatant was recentrifuged (54000 x g; 60 min.), and the pellets were then rehomogenzied to yield a "crude enzyme preparation." For further purification, sodium deoxycholate was added. This was followed by centrifugation and dialysis, filtration through a fine pore filter paper (Whatman brand No. 1 filter paper), and fractionation on DEAE-cellulose columns, as is shown in Lanzillo and Fanburg, *Biochemistry* 16, 5491-5495 (1977), referred to above.

Fractions from the columns were assayed for ACE activity. The most positive fractions were pooled for use as a "partially purified enzyme preparation." ACE activity was measured by using (as substrate) radiolabeled diglycyl hippurate ($[^3H]$Hip-Gly-Gly, obtained from Ventrex Laboratories, Portland, Me.). ACE activity was assessed by separating the radioactive peptide on the basis of its differential solubility in ethyl acetate. Where general mention is made below of measuring for ACE activity, this same technique was used. Both the crude and partially purified enzyme preparations were used as inoculum antigens, as is set forth below.

Immunization of Mice

BALB/cAu mice were selected for immunization. They were immunized with 0.1 ml of a 1:1 mixture of the crude enzyme preparation and Freund's incomplete adjuvant, injected intraperitoneally. The mice were restimulated with 0.1 ml of the partially purified enzyme preparation. Four days later, the mice were killed and their spleens removed for use.

Hybridization and Hybridoma Culture Methods

The spleen cells from the immunized mice were fused with myeloma cells using the method of Kohler and Milstein, *Eur. J. Immunol.* 6, 511–519 (1976). The myeloma cells used were NS-1(P3 NS1 Ag4/1) cells that were originally obtained from the Salk Institute and maintained in conventional Dulbecco's modified Eagle's minimal essential medium (hereinafter "DME medium") with 10% fetal bovine serum. The spleen cell/myeloma ratio was 10:1. Fusion was effected with 40% polyethylene glycol ($M_r$ 1050). Fused cells were selected in hypozanthine/amethopterin/thymidine medium. They were then cultured further in hypozanthine/thymidine medium. By this means selection was made only for successfully fused cells. Soft agar cloning techniques were used, as described by Coffino, Laskov, and Scharff, Science 167, 186–188 (1970).

Screening

Following the hybridization process disclosed above, 960 microwell cultures (10 Linbro plates) were prepared, containing the media in which the hybrid cells were held. Virtually all culture wells showed a growth of hybrid cells at the end of a two-week culture period. As a primary screen, the supernatants produced by these hybrid cells were tested for binding to bovine pulmonary vein endothelial cells, by the method disclosed below. Cells from nine of the microwells were selected for expansion on the basis of reactivity detected in the test. After further culturing, the cells were retested by the same means. One hybridoma supernatant appeared particularly active. Therefore cells from this hybridoma were chosen for ultimate expansion and cloning. Cloned cells were also used in the production of ascites by conventional injection of cells into pristane-treated BALB/cAu mice. The hybridoma has been deposited at the American Type Culture Collection and has been assigned the designation: HB 8191. For clarity, this particular hybridoma will be referred to hereinafter by that designation.

Tests for Binding

ELISAs were used to conduct the tests for binding to bovine pulmonary vein endothelial cells that were used as the primary screening referred to above, as well as certain other tests to be discussed below of specificity and cross-species activity. The basic ELISA method used was one well known in the art and disclosed in Engvall and Pesce, eds. Quantitative Enzyme Immunoassay. *Scand. J. Immunol.*, suppl. 7 (1978). In the ELISA method used, the antigen is bound onto an adsorbtor substrate, of which many are well known to one skilled in the art. Typically a 96-well Linbro microtiter plate is used, and in the disclosure below will be used as a typical and illustrative example of a receptor substrate. In the event the antigen is expressed on a cell, the cell itself may be permitted to bind to the plate and may be cultured on the plate.

The wells bearing the test antigen are then overlayed with a first antibody specific to the antigen to be detected, thereby exposing the test antigen to the antibody. In other applications, the antigen is known and an antibody of unknown characteristics is applied to it as the first antibody. The amounts of the first antibody that remain unbound to the test antigen are washed off or otherwise removed. The material remaining on the plate is then exposed to a marker-coupled antibody specific to the animal that produced the first antibody. The marker may be a fluorescent or a radioactive material but commonly is an enzyme, the function of which will be discussed below. Thus, if the first antibody had been made by a mouse, the marker-coupled antibody could be an enzyme-coupled anti-mouse antibody, such as commercially available goat anti-mouse antibody labeled with alkaline phosphatase.

If any of the first antibody became bound to the test antigen, so that it was not removed with the unbound first antibody, the marker antibody will attach to it. Next, unbound amounts of the marker antibody are washed off or otherwise removed. A substrate is then added specific for the enzyme that is linked to the marker antibody. The enzyme linked to the marker antibody that in turn has become bound to the first antibody is then allowed to react with the substrate to produce a detectable change in the substrate. Typically, an enzyme-substrate system is enployed such that, upon reaction of the enzyme with the substrate, the ability of the solution containing the substrate to absorb light is changed. The action of the enzyme on the substrate is then stopped by the addition of an appropriate inhibitor. Finally, the extent of the reaction is measured by observing the change in the substrate. The amount of reaction is related to the amount of enzyme present, the amount of enzyme present is related to the amount of marker antibody bound, and the amount of marker antibody bound in turn is related to the amount of first antibody bound. Finally, the amount of first antibody bound is related to the amount of antigen present. Thus, by this process, both the presence and the amount of antigen can be measured.

It is possible to combine some of the ELISA steps reviewed above. Thus, the first antibody may be itself marked, for example by linking an enzyme to it. By this means, the need for a separate marker enzyme may be eliminated. Likewise, some markers do not require the stopping of the reaction by addition of appropriate inhibitors.

By Ouchterlony tests, HB 8191 was found to be a clone producing IgM antibodies. Therefore, another IgM producing hybridoma prepared against an unrelated antigen, α-trinitrophenyl, was used as a control in the specificity testing. Cell cultures used in the various ELISAs included cultures of the endothelial cells from adult bovine adrenal gland, aorta, pulmonary vein, and retina, from fetal bovine aorta and ovary, and from mouse brain and epididymal fat pad. These cell cultures were obtained by following protocols published in the following works. See Folkman, Haudenschild, and Zetter, *Proc. Natl. Acad. Sci. U.S.A.* 76, 5217–5221 (1979); Booyse, Sedlak, and Rafelson, *Thromb. Diath. Haemorrh.* 34, 825–839 (1975); Jaffe, Nachman, Becker, and Minick, *J. Clin. Invest.* 52, 2745–2756 (1973); Ryan, Chung, Martin, and Ryan, Tissue Cell 10, 535–554 (1978); Schwartz, *In Vitro* 12, 966–980 (1978); DeBault, Kahn, Frommes, and Cancilla, In Vitro 15, 473–487 (1979); and Wagner and Matthews, *Microvasc. Res.* 10, 286–297 (1975). Other conventional cell cultures used in the ELISAs (the suppliers thereof noted in parentheses) included human Ruba endothelial cells (Reznikoff as discussed in Reznikoff and DeMars, *Cancer Res.* 41,1141–1126, 1981), adult bovine turbinate cells and bovine fetal lung fibroblasts (C. Kanitz), fetal bovine heart endothelial cells (American Type Culture Collection), human and mouse embryo fibroblast lines (B. Kahan), and L929 mouse fibroblasts (E. Borden).

In the ELISAs, selected test endothelial or control fibroblast cells were permitted to grow to confluency in 96-well Linbro plates. Fetal bovine serum is customarily used in the culture of such cells. However, fetal bovine serum contains bovine ACE. To avoid incidental binding of such ACE and resulting invalidation of the tests, cells were grown in serum-free DME medium for 24–48 hours before use in ELISAs. Cells were fixed in 0.02% glutaraldehyde, and 0.3% gelatin was added during washing procedures to decrease nonspecific adsorbtion. The response of the cells to exposure to test material was measured by using a dual wavelength Microelisa Reader manufactured by Dynatech, Alexandria, Va.

Specificity testing also included flow cytometry employing a fluorescence-activated cell sorter equipped with a 5-watt argon ion laser tuned to 488 nm and operating at a 100 mW output. Cells were passed through a 70 μm orifice and assessed for relative intensity of fluorescence emmission at levels above 515 nm, as well as forward angle light scatter. Cells were sorted into DME medium with 1% bovine serum albumin for ACE assays or into tumor-conditioned medium for endothelial cell culture.

Cells to be examined using flow cytometry were obtained by collagenase treatment of the source material. They were washed in DME medium and then passed through 15 to 240 μm filters of the Nytex brand. They were then centrifuged through a selected specific gravity interface by carefully layering the cells suspended in DME medium above a layer of a second medium of higher specific gravity. Such mediums are commercially available and well known in the art. The medium sold under the trade name Ficoll-Hypaque was employed. The cells retained in the DME medium were incubated at room temperature for 30 minutes with serum diluted in $CA^{2+}$ and $Mg^{2+}$-free phosphate buffered saline containing 1% bovine serum albumin and 1% sodium azide. This time was found sufficient for any antibodies in the serum to react with the cells. The cells were then washed again in 1% bovine serum albumin and incubated with fluorescein isothiocyanate-labeled rabbit anti-mouse immunoglobulin (obtained from Cappel Laboratories, Cochranville, Pa.). The cells were then washed again and diluted to $2 \times 10^5 - 1 \times 10^6$ cells per ml with the phosphate buffered saline solution referred to above. For viable, sterile sorting, the final cell suspension was diluted with the phosphate buffered saline solution also containing 2% fetal bovine serum.

Immunohistological testing for specificity was also employed. Cells from culture were grown directly on cover slips. When uncultured tissue was examined, cryostat sections were cut at 6 μm and placed on cover slips for processing. The cryostat sections were used unstained or, alternatively, were stained with hematoxylin in water for five minutes. Cells from culture always were examined unstained.

Table 1 shows the binding of antibodies contained in HB 8191 ascites fluid to the indicated cultured cell lines, fresh isolates, or cryostat sections, together with the results for separate assay for ACE activity in those materials. ACE activity was independently measured by the use of radiolabeled diglycyl hippurate, disclosed above. Cells are referred to as "early passage" in the table if they had been grown to confluence and transferred to new culture dishes fewer than ten times. "Late passage" cells are those that had been transferred more than 16 times. It is generally known that late passage cells at some point lose many of their normal cell surface antigens as is reflected in the lack of ACE activity shown for late passage cells in Table 1.

TABLE 1

| Source of cells | ELISA | Flow cytometry | Immuno-histology | ACE activity |
|---|---|---|---|---|
| Endothelium | | | | |
| Adult bovine aortic endothelium | | | | |
| Fresh isolate | + | + | NT | + |
| Early passage | + | + | + | + |
| Late passage | − | − | NT | − |
| Fetal bovine aortic | | | | |
| Fresh isolate | NT | + | NT | + |
| Early passage | + | + | + | + |
| Adult bovine adrenal capillary | | | | |
| Fresh isolate | + | + | NT | + |
| Early passage | + | + | NT | + |
| Late passage | − | − | NT | − |
| Adult bovine retinal | + | NT | + | + |
| Mouse epididymal fat pad | NT | + | + | + |
| Mouse brain | | | | |
| Early passage | + | + | + | + |
| Late passage | − | − | NT | − |
| Human Ruba | | | | |
| (endothelial cells) | + | NT | NT | + |
| Human umbilical vein | NT | + | + | NT |
| Fibroblasts | | | | |
| Bovine turbinate | + | − | NT | NT |
| Bovine fetal lung | − | NT | NT | NT |
| Mouse embryo | NT | − | NT | NT |
| Mouse L929 | − | − | − | − |
| Human foreskin | − | NT | NT | − |
| Human lung | − | NT | NT | − |
| Other* | | | | |
| Mouse adrenal gland | | | | |
| Endothelial cells | | | + | |
| Nonendothelial cells | | | − | |
| Mouse kidney | | | | |
| Endothelial cells | | | + | |
| Proximal tubules | | | + | |
| Other cell types | | | − | |
| Human umbilical vein | | | | |
| Endothelial cells | | | + | |
| Subendothelial region | | | + | |
| Other nonendothelial cells | | | − | |

NT, not tested.
*Cryostat sections.

As may be seen by examination of Table 1, antibodies produced by HB 8191 were specific to ACE activity found in both adult and fetal bovine materials, mouse materials, and human materials from various tissues, whether fresh material or derived from cell culture. ELISAs were positive on endothelial cells when performed with either ascites fluid or cell culture medium supernatants. Nonendothelial cells such as mouse L929 fibroblasts were negative, as were human foreskin fibroblasts and bovine fetal lung fibroblasts. The only inconsistent results were obtained with the bovine turbinate cell line, which was positive in ELISAs but was negative both for enzyme activity and flow cytometry.

A direct test for specificity of the antibody was carried out by adsorbing purified ACE prepared from bovine fetal lung material unto microtiter wells for ELISAs. Activity of ascites fluid was seen at dilutions ranging from 1:100 to 1:10,000, depending upon the preparation. Ascites fluid developed from HB 8191 cells was always active at dilutions two or more powers of 10 higher than the ascites fluid used as a control and made from the hybridoma prepared against the unrelated antigen referred to above.

It was determined that the ability of HB 8191 produced antibody to bind to the surface of endothelial cells allows the antibody to be used both for the identification of such cells and for their isolation. Isolated endothelial cells have experimental utility but also are used for other purposes, such as to seed artificial vascular grafts. The cells grow within the artificial grafts to produce a vascular lining that is immunologically similar to natural vascular materials. Cell sorting was conducted with a fluorescence-activated cell sorter, as is disclosed above. For demonstration purposes, adult bovine aortic endothelial cells and mouse L929 fibroblasts were used. Sorting parameters were so set that "bright" cells included 25% of fibroblasts and 50% of endothelial cells, whereas "dim" cells included 50% of fibroblasts and 20% of endothelial cells. The two cell suspensions then were mixed as a test, and collections of dim and bright cells were obtained by sorting. ACE activity in the dim and bright cell populations was then measured by the ACE assay referred to above. The results established that the bright cells, labeled with HB 8191 antibody, had ACE activity, whereas the dim, unlabeled cells had low or no ACE activity.

As a separate test, cell suspensions were prepared from freshly obtained bovine adrenal cortex. After labeling with anti-ACE antibody obtained from HB 8191, cell sorting was carried out by selecting out the brightest 25% and dimmest 25% of cells in the suspension. Bright cells were found to be enriched for ACE activity, whereas activity in dim cells was decreased when compared to the original cell preparation. Cells from the sorted groups were then cultured. Both dim and bright cells suspensions gave rise to cultures that grew to confluency. The bright cell cultures appeared to be enriched for endothelial cells, as judged by gross microscopic inspection, by continued ACE activity (assayed as above), and by successful in vitro passage.

The ability of HB 8191 antibody preparations successfully to distinquish endothelial cells both for purposes of identification and for isolation for in vitro cultivation was thus successfully shown with the use of flow cytometry. From the results of the flow cytometry testing it may be reliably predicted that "panning" or selective adhesion to antibody-coated dishes, as taught by Mage, McHugh, and Rothstein, J. Immunol. Methods 15, 47–56 (1977), and alternative immunological isolation procedures, such as those taught by Fong, et al. J. Immunol. Methods 46, 153–163 (1981) should be equally feasible. In all of these methods, an antibody specific to an antigen expressed by a cell is adhered to a selected adsorbtor substrate, such as a glass or plastic surface or gel beads of sorts well known in the art such as those sold under the trademark "AFFI-GEL 10" by the Bio-Rad Company. A preparation of cells is then exposed to the antibody-bearing substrate. Cells expressing the antigen to which the antibody is specific are bound to the antibody and held to the substrate while the remainder of the cells are washed away. The bound cells may then be collected.

The antibody obtained from HB 8191 was found to successfully identify ACE separate from any endothelial cells in the ELISA assays discussed above. In addition, antibody from HB 8191 was used by the ELISA method discussed above to quantitatively measure ACE isolated from lung tissue. The ACE level in serum has also been determined by ELISA tests in which serum containing ACE was used as the antigen bound to the substrate. As is discussed in Ryan, et al., U.S. Pat. No. 4,115,374, detection of the presence and levels of ACE in serum and urine by reliable and sensitive means has utility as a medical diagnostic tool. Dilutions of the serum were used, and the antibody obtained from HB 8191 was then used to determine the presence and amounts of ACE.

More particularly, serial dilutions of fresh serum were made. 100 $\mu$l of the diluted samples were placed into individual wells of a conventional microtiter plate. 96 well Linbro plates were found to be satisfactory. Duplicates were run at each dilution. After overnight exposure of the microtiter plates to the samples, the wells were rinsed with phosphate-buffered saline. The wells were then overlain with a 1:1000 dilution of anti-ACE antibody produced by HB 8191. For a specificity control, the whole procedure also was run, in duplicate, using the anti-$\alpha$-trinitrophenyl monoclonal antibody discussed above.

After incubation with the antibodies, ELISA tests were completed, as described above. A phosphatase-labeled rabbit anti-mouse antibody was used as a marker antibody. Evaluation of the ELISA reaction in the various dilutions demonstrated that quantitative determination of the amount of ACE present in the initial serum sample had been achieved. Since the marker is quantitatively associated with the marker antibody, which is quantitatively associated with the monoclonal antibody, which in turn is quantitatively associated with the ACE present, the amount of bound marker is proportional to the amount of ACE. The same would be true if the monoclonal antibody were itself marked. Identification of the amount of ACE in a sample of unknown ACE concentration could be determined by comparison of the reaction of a selected dilution of the sample with the reaction of a sample having a known concentration of ACE. Such quantitative assay procedures are well known in the art.

Although only a single hybridoma producing a single monoclonal antibody is described, it is contemplated that the present invention encompasses the method generally of making monoclonal antibodies of improved cross-species specificity, as it is disclosed above.

What is claimed is:

1. A method for preparing a monoclonal antibody of improved cross-species specificity comprising the steps of:
   (a) preparing angiotesin-converting enzyme as an inoculum antigen from a first species of animal producing the antigen;
   (b) immunizing a selected subject animal with the inoculum antigen;
   (c) fusing spleen cells from the immunized subject animal with myeloma cells to produce hybridomas, and culturing the hybridomas;
   (d) preparing a test antigen corresponding to the inoculum antigen but derived from a second species of animal different from the first species of animal from which the inoculum antigen was prepared;
   (e) screening the hybridomas for desired antibody production against the test antigen;
   (f) culturing the hybridoma producing antibody most active against the test antigen; and
   (g) producing a monoclonal antibody from the hybridoma.

2. The method of claim 1 wherein the inoculum antigen is an angiotensin-converting enzyme and the test antigen is endothelial cells bearing angiotensin-converting enzyme.

3. The method of claim 1 wherein the inoculum antigen is a preparation of angiotensin-converting enzyme from rat tissue and the test antigen is bovine endothelial cells expressing angiotensin-converting enzyme on their cell surface.

4. A method of preparing monoclonal antibody that reacts both with purified angiotensin-converting enzyme and mouse, bovine, and human endothelial cells, which comprises culturing the hybridoma ATCC HB 8191 in a suitable medium and recovering the antibody from the supernatant above the hybridoma.

5. The monoclonal antibody prepared by the method of claim 4.

6. A method of preparing monoclonal antibody that reacts both with purified angiotensin-converting enzyme and mouse, bovine, and human endothelial cells, which comprises injecting into a mouse the hybridoma ATCC HB 8191 and recovering the antibody from one of the malignant ascites and the serum of the mouse.

7. The monoclonal antibody prepared by the method of claim 6.

8. A monoclonal antibody of class IgM produced by a hybridoma formed by fusion of cells from a mouse myeloma line and spleen cells from a mouse previously immunized with angiotensin-converting enzyme taken from endothelial cells, which antibody reacts both with purified angiotension-converting enzyme and mouse, bovine, and human endothelial cells.

9. The monoclonal antibody of claim 8 wherein the hybridoma was formed by fusion by NS-1(P3 NS1 Ag4/1) myeloma cells and spleen cells from a BALB/c mouse previously immunized with an angiotensin-converting enzyme preparation made from rat tissue containing endothelial cells.

10. The monoclonal antibody of claim 9 wherein the hybridoma was screened for antibody production against angiotensin-converting enzyme produced by a species other than the rat.

11. The monoclonal antibody of claim 9 wherein the hybridoma was screened for antibody production against endothelial cells bearing angiotensin-converting enzyme taken from a species other than the rat.

12. The monoclonal antibody of claim 11 wherein the endothelial cells bearing angiotensin-converting enzyme taken from a species other than the rat are bovine endothelial cells.

13. A method of sorting viable endothelial cells from a sample of cellular tissue containing endothelial cells, comprising the steps of:
   (a) incubating cells from the sample with monoclonal antibody produced by the hybridoma ATCC HB 8191 to bind the monoclonal antibody to endothelial cells in the sample; and
   (b) sorting the cells by means reactive to the presence of the monoclonal antibody, retaining cells bound thereto.

14. The method of claim 13 including, following the step of incubating cells from the sample with monoclonal antibody, the step of incubating the cells with a marker-labeled anti-mouse antibody to bind the marker-labeled antibody to the monoclonal antibody that is bound to the endothelial cells; and wherein the step of sorting the cells by means reactive to the presence of the monoclonal antibody includes sorting the cells by means reactive to the presence of the marker.

15. The method of claim 14 wherein the marker is an enzyme.

16. The method of claim 14 wherein the marker is a fluorescent material.

17. The method of claim 14 wherein the marker is a radioactive material.

18. A method of sorting viable endothelial cells from a sample of cellular tissue containing endothelial cells, comprising the steps of:
   (a) incubating cells from the sample with the monoclonal antibody of claim 8 to bind the antibody to endothelial cells in the sample; and
   (b) sorting the cells by means reactive to the presence of the monoclonal antibody, retaining the cells marked therewith.

19. The method of claim 18 including, following the step of incubating cells from the sample with monoclonal antibody, the step of incubating the cells with a marker-labeled anti-mouse antibody to bind the marker-labeled antibody to the monoclonal antibody that is bound to the endothelial cells; and wherein the step of sorting the cells by means reactive to the presence of the monoclonal antibody includes sorting the cells by means reactive to the presence of the marker.

20. The method of claim 19 wherein the marker is an enzyme.

21. The method of claim 19 wherein the marker is a fluorescent material.

22. The method of claim 19 wherein the marker is a radioactive material.

23. A method of sorting viable endothelial cells from a sample of cellular tissue containing endothelial cells, comprising the steps of:
   (a) exposing a selected adsorbtor substrate to monoclonal antibody produced by the hybridoma ATCC HB 8191 to adsorb the antibody onto the adsorbtor substrate;
   (b) exposing the adsorbed antibody to cells from the sample to allow the endothelial cells to become bound to the antibody;
   (c) removing cells not bound to the antibody; and
   (d) collecting the cells bound to the antibody.

24. A method of sorting viable endothelial cells from a sample of cellular tissue containing endothelial cells, comprising the steps of:

(a) exposing a selected adsorbtor substrate to the monoclonal antibody of claim 8 to adsorb the antibody onto the adsorbtor substrate;
(b) exposing the adsorbed antibody to cells from the sample to allow the endothelial cells to become bound to the antibody;
(c) removing cells not bound to the antibody; and
(d) collecting the cells bound to the antibody.

25. A method of assaying for the presence of angiotensin-converting enzyme in a sample of test material, comprising the steps of:
   (a) binding the test material to an adsorbtor substrate;
   (b) exposing the test material to monoclonal antibody produced by the hybridoma ATCC HB 8191 to allow the antibody to bind to any angiotensin-converting enzyme present in the test material;
   (c) removing the unbound portion of the monoclonal antibody; and
   (d) assaying for the presence of bound monoclonal antibody.

26. The method of assaying for the presence of angiotensin-converting enzyme in a sample of test material specified in claim 25 wherein the step of assaying for the presence of bound monoclonal antibody includes:
   (a) exposing the test material and bound monoclonal antibody to a marker-coupled anti-mouse antibody to allow the marker-coupled antibody to bind to any monoclonal antibody bound to the test material;
   (b) removing the unbound portion of the marker-coupled antibody; and
   (c) measuring the amount of marker remaining on the test material.

27. The method of claim 26, wherein the marker is an enzyme.

28. The method of claim 26, wherein the marker is a fluorescent material.

29. The method of claim 26, wherein the marker is a radioactive material.

30. The method of claim 25 wherein a known dilution of test material is used and wherein the step of assaying for the presence of bound monoclonal antibody includes measuring the amount of a marker quantitatively associated with the antibody by means of a reaction that may be quantitatively measured and that can be compared with the comparable reactions of known amounts of angiotensin-converting enzyme bound to the monoclonal antibody, whereby the assay for the presence of angiotensin-converting enzyme may be a quantitative assay.

31. A method of assaying for the presence of angiotensin-converting enzyme in a sample of test material, comprising the steps of:
   (a) binding the test material to an adsorbtor substrate;
   (b) exposing the test material to the monoclonal antibody of claim 8 to allow the antibody to bind to any angiotensin-converting enzyme present in the test material;
   (c) removing the unbound portion of the monoclonal antibody; and
   (d) assaying for the presence of bound monoclonal antibody.

32. The method of assaying for the presence of angiotensin-converting enzyme in a sample of test material specified in claim 31 wherein the step of assaying for the presence of bound monoclonal antibody includes:
   (a) exposing the test material and bound monoclonal antibody to a marker-coupled anti-mouse antibody to allow the marker-coupled antibody to bind to any monoclonal antibody bound to the test material;
   (b) removing the unbound portion of the marker-coupled antibody; and
   (c) measuring the amount of marker remaining on the test material.

33. The method of claim 32, wherein the marker is an enzyme.

34. The method of claim 32, wherein the marker is a fluorescent material.

35. The method of claim 32, wherein the marker is a radioactive material.

36. The method of claim 31 wherein a known dilution of test material is used and wherein the step of assaying for the presence of bound monoclonal antibody includes measuring the amount of a marker quantitatively associated with the antibody by means of a reaction that may be quantitatively measured and that can be compared with the comparable reactions of known amounts of angiotensin-converting enzyme bound to the monoclonal antibody, whereby the assay for the presence of angiotensin-converting enzyme may be a quantitative assay.

37. A method of assaying for the presence of angiotensin-converting enzyme in a sample of test material comprising the steps of:
   (a) binding the test material to an adsorbtor substrate;
   (b) coupling a marker to the monoclonal antibody produced by hybridoma ATCC HB 8191;
   (c) exposing the test material to the monoclonal antibody so coupled to allow the monoclonal antibody to bind to any angiotensin-converting enzyme present in the test material;
   (d) removing the unbound portion of the monoclonal antibody;
   (e) measuring the amount of marker remaining on the test material.

38. The method of claim 37, wherein the marker is an enzyme.

39. The method of claim 37, wherein the marker is a fluorescent material.

40. The method of claim 37, wherein the marker is a radioactive material.

41. The method of claim 37 wherein a known dilution of test material is used and the marker is quantitatively coupled to the monoclonal antibody, and wherein the step of measuring the amount of marker remaining on the test material includes measuring the amount of marker by means of a reaction that may be quantitatively measured and that can be compared with the comparable reactions of known amounts of angiotensin-converting enzyme bound to the monoclonal antibody, whereby the assay for the presence of angiotensin-converting enzyme may be a quantitative assay.

42. A method of assaying for the presence of angiotensin-converting enzyme in a sample of test material comprising the steps of:
   (a) binding the test material to an adsorbtor substrate;
   (b) coupling a marker to the monoclonal antibody of claim 8 produced by hybridoma ATCC HB 8191;
   (c) exposing the test material to the monoclonal antibody so coupled to allow the monoclonal antibody to bind to any angiotensin-converting enzyme present in the test material;
   (d) removing the unbound portion of the monoclonal antibody;

(e) measuring the amount of marker remaining on the test material.

43. The method of claim 42, wherein the marker is an enzyme.

44. The method of claim 42, wherein the marker is a fluorescent material.

45. The method of claim 42, wherein the marker is a radioactive material.

46. The method of claim 42 wherein a known dilution of test material is used and the marker is quantitatively coupled to the monoclonal antibody, and wherein the step of measuring the amount of marker remaining on the test material includes measuring the amount of marker by means of a reaction that may be quantitatively measured and that can be compared with the comparable reactions of known amounts of angiotensin-converting enzyme bound to the monoclonal antibody, whereby the assay for the presence of angiotensin-converting enzyme may be a quantitative assay.

47. The hybridoma ATCC HB 8191.

* * * * *